United States Patent [19]

La Rosa

[11] 4,227,534

[45] Oct. 14, 1980

[54] SELF-INFLATING URINARY CATHETER

[75] Inventor: John F. La Rosa, West Kingston, R.I.

[73] Assignee: International Paper Company, New York, N.Y.

[21] Appl. No.: 34,937

[22] Filed: Apr. 30, 1979

[51] Int. Cl.³ ............................................. A61M 25/00
[52] U.S. Cl. .............................................. 128/349 B
[58] Field of Search ............ 128/348, 349 B, 349 BV

[56] References Cited

U.S. PATENT DOCUMENTS

| | | | |
|---|---|---|---|
| 3,044,468 | 7/1962 | Birtwell | 128/349 B |
| 3,154,078 | 10/1964 | Goodrich, Jr. | 128/348 |
| 4,016,885 | 4/1977 | Bruner | 128/349 B |
| 4,074,714 | 2/1978 | Binard et al. | 128/218 P |

Primary Examiner—John D. Yasko
Attorney, Agent, or Firm—Robert R. Jackson; Charles B. Smith

[57] ABSTRACT

A self-inflating urinary catheter which includes a retention balloon has a fluid-filled, unpressurized, deformable reservoir communicating with the balloon. An elastic diaphragm is arranged to squeeze the reservoir against another surface so as to pressurize the fluid, thereby exerting force to expel the fluid from the reservoir to inflate the retention balloon.

11 Claims, 7 Drawing Figures

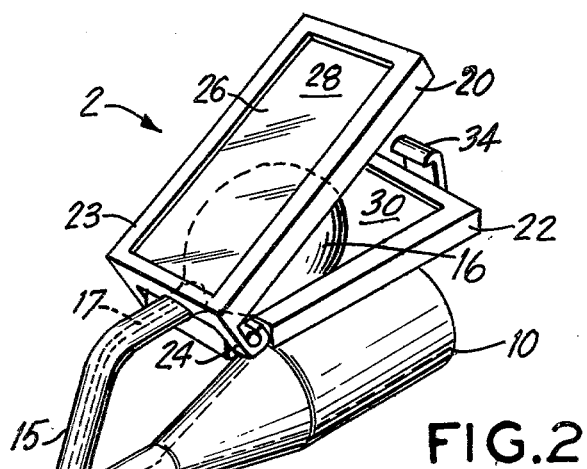
FIG.2
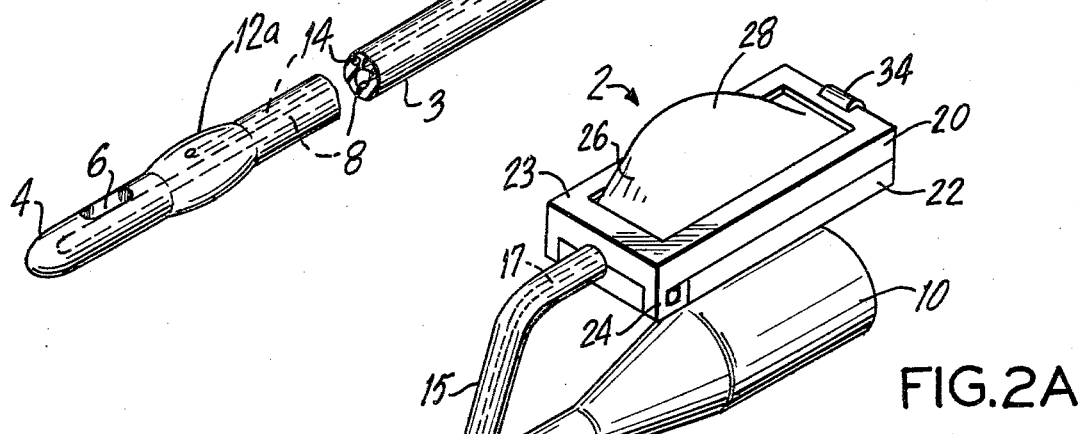
FIG.2A
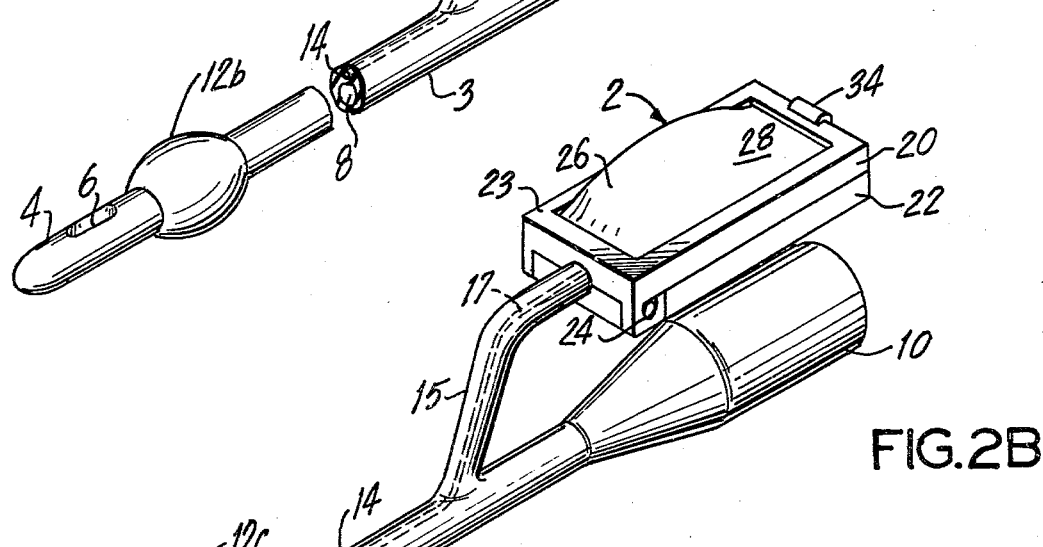
FIG.2B
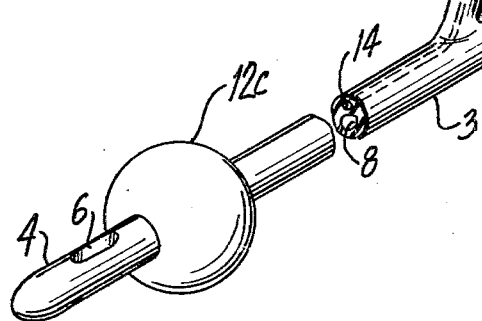

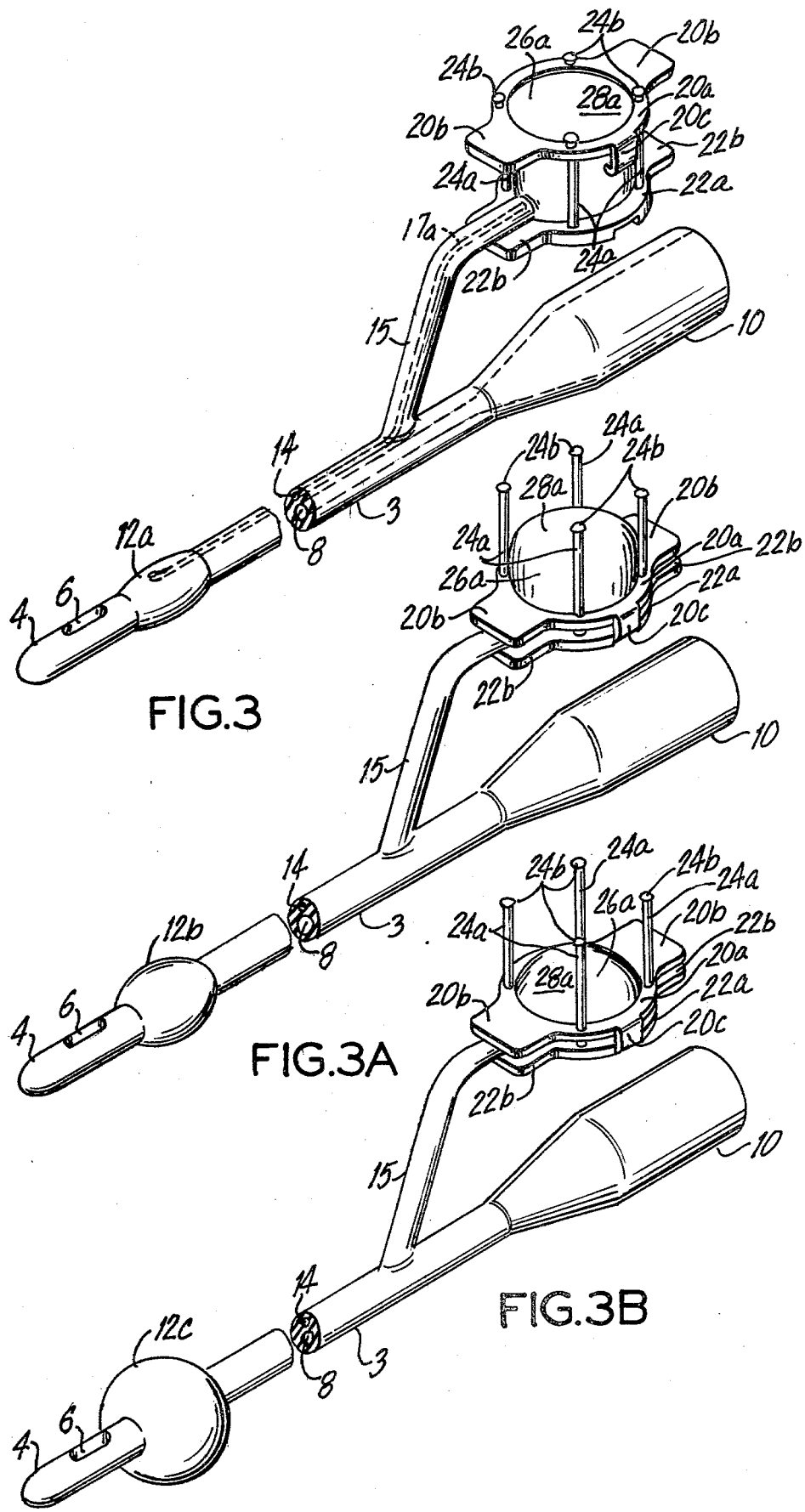

4,227,534

SELF-INFLATING URINARY CATHETER

BACKGROUND OF THE INVENTION

The retention of a urinary catheter in a human bladder so as to prevent it from slipping out during the long period required to drain the bladder has been accomplished in several ways. The generally accepted so-called "Foley catheter" has a small inflatable balloon at its distal end (the end which is inserted) which is inflated to hold the distal end inside the bladder after the distal end has been inserted safely through the urethra and into the bladder. Inflation is accomplished by pumping a fluid into the balloon through an inflation lumen, a passage in the shaft of the catheter parallel to the drainage lumen or passage. The inflation fluid may be a gas or a liquid such as distilled water.

Current methods of inflating the balloon are susceptible to over- or under-inflation. Methods and devices for inserting the catheter and inflating the balloon are cumbersome and complicated. For instance, one such procedure is to insert the distal end of the catheter through the urethra into the bladder and at the same time to insert a syringe needle into the inflation lumen and then squeeze the syringe to inflate the balloon. This may require an operator and an assistant and may result in trauma to the patient if the balloon is inadvertently inflated while it is still within the urethra.

With any Foley type catheter, means also have to be provided for deflating the retention balloon after use. Again, the deflation systems in present use are sometimes too complicated. This is often the case when the inflating device is a syringe and needle inserted into the inflation lumen. Deflation will again require such insertion of the syringe to withdraw fluid. This may also be a two-handed operation, requiring a second person to hold the catheter.

So-called self-inflating catheters were developed to try to solve these problems, but they have had problems of their own. A number of arrangements have been tried to provide a reservoir, integral with the catheter, for storage of inflation fluid under pressure ready to be expelled to inflate the retention balloon. But such systems have not thus far met the requirements for satisfactory performance.

These requirements are that the catheter have a long shelf-life under sanitary conditions, that it be immediately ready for use, that it be simple to operate by one person and that it be inexpensive to produce as a throw-away item. Its arrangement must also be such that the retention balloon is capable of deflation and reinflation if the instrument is prematurely inflated before its desired placement with the distal end in the bladder.

A widely used type of self-inflating catheter has an over-inflated rubber reservoir in which the fluid is retained by a clamp under pressure during storage. After insertion of the catheter into the bladder, the clamp is removed to allow the reservoir to deflate and thereby inflate the retention balloon. During storage of such catheters, however, the stretched reservoir walls tend to lose their restoring forces because they "take a set" and "lose memory" so that when the clamp is removed the rubber reservoir does not exert enough force to inflate the balloon. Also, once such a system is activated to inflate the retention balloon, there is no way of deflating and reinflating the balloon in case the catheter is not properly placed in the first instance. There is also no adequate way of determining how much of the fluid has been dispersed from the reservoir at any instant. Another problem is that when the fluid is thus stored under pressure, considerable loss of fluid may occur as a result of penetration of fluid vapor through the stretched reservoir walls. This reduces the amount by which the retention balloon may be inflated, and in some cases so much fluid is lost that no inflation occurs in use.

The principal objects of this invention are therefore to provide in an inexpensive urinary catheter a retention balloon inflation system in which no fluid loss occurs, which will allow the retention balloon to be deflated and reinflated and which will provide a visual indicator of the degree of inflation at any instant.

SUMMARY OF THE INVENTION

These and other objects of the invention are accomplished by providing a self-inflating catheter having a resilient and deformable fluid reservoir at or near its proximal end (the end of the catheter which is opposite the distal end) connected through a restricted passage and the inflation lumen to the retention balloon which is at the distal end to be inserted into the patient's bladder. The inflation lumen is a passage in the shaft of the catheter running parallel to the drainage lumen which is the main passage in the shaft of the catheter through which the fluid is drained from the bladder into a suitable receptacle outside of the patient.

Prior to use, the reservoir contains fluid in an unpressurized state and in sufficient quantity so that when the reservoir is squeezed the fluid is expelled through the restricted passage and through the inflation lumen to inflate the retention balloon. The purpose of the restricted passage is to provide an elapse of time between the initial squeezing of the reservoir and the completion of expulsion of the fluid from the reservoir into the balloon.

An elastic membrane or diaphragm, these terms herein being used interchangeably, formed preferably substantially flat, is arranged to squeeze the reservoir against another surface with sufficient force ultimately to expel the fluid and inflate the retention balloon. The other surface may be another similar membrane or it may be a substantially rigid surface.

Further features of the invention, its nature, and various advantages will be more apparent from the accompanying drawing and the following detailed description of the invention.

BRIEF DESCRIPTION OF THE DRAWING

FIG. 2 is a partly fragmented perspective view showing one embodiment of the inflation apparatus of this invention with the reservoir and diaphragm in a relaxed unpressurized condition and with the retention balloon deflated prior to insertion of the catheter.

FIG. 2A is a view similar to FIG. 2 showing the diaphragm squeezing the reservoir and the retention balloon commencing to inflate.

FIG. 2B is a view similar to FIG. 2 with the fluid expelled fom the reservoir, the diaphragm substantially contracted back into its original flat shape and with the retention balloon inflated.

FIG. 3 is a partly fragmented perspective view showing another embodiment of the inflation apparatus of this invention with the reservoir and diaphragm relaxed and unpressurized and with the retention balloon deflated.

FIG. 3A is a view similar to FIG. 3 showing the diaphragm squeezing the reservoir into a pressurized condition and with the retention balloon commencing to inflate.

FIG. 3B is a view similar to FIG. 3 with the fluid expelled from the reservoir, the diaphragm substantially contracted back into its original flat shape and with the retention balloon inflated.

DETAILED DESCRIPTION OF THE INVENTION

Figure 1:
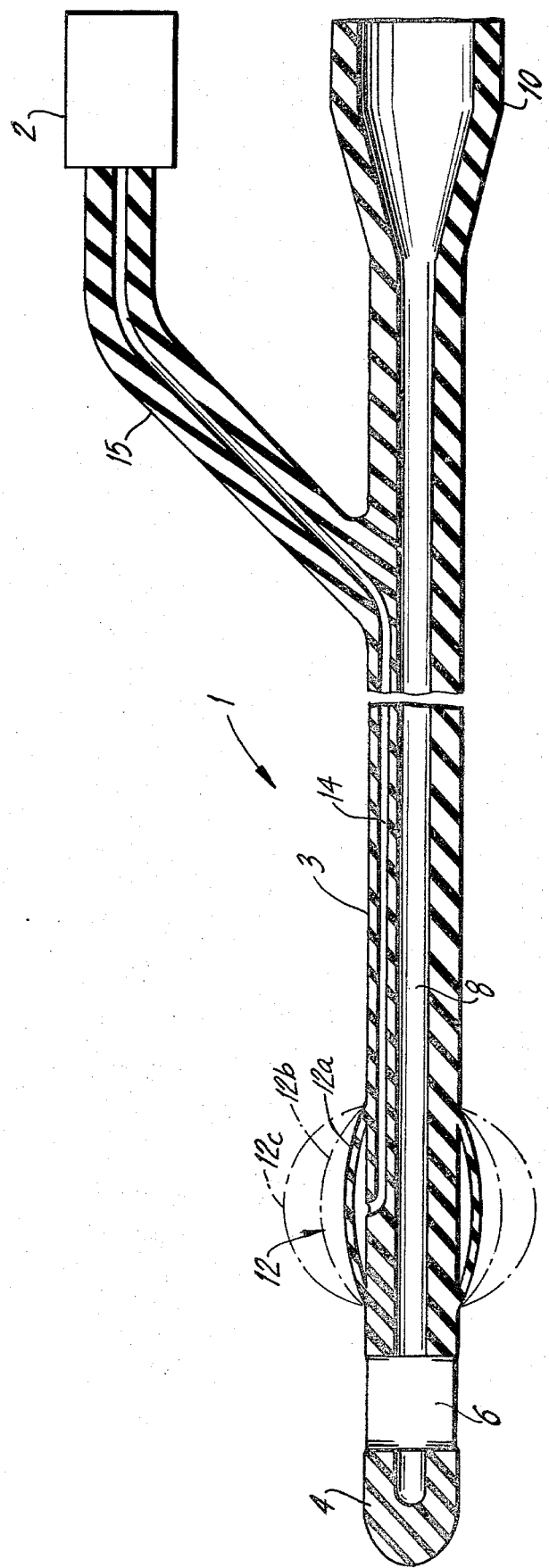
FIG. 1 is a longitudinal, partly fragmentary, sectional view of a self-inflating catheter of which the present invention is an improvement, with the improved part indicated schematically to show general relationships.

A self-inflating urinary catheter of the type of which this invention is an improvement is indicated at 1 in FIG. 1. The improved inflation apparatus of the invention is indicated schematically at 2 and its details and various forms will be further described and shown.

The catheter shown in FIG. 1 is the "Foley catheter" mentioned above. It comprises a long narrow resilient cylindrical shaft 3 made of latex or silicone rubber and with one end 4, the distal end, rounded off. This is to facilitate its insertion into and through the urethra and into the bladder of the patient for the purpose of draining fluids from the bladder which have become blocked or dammed up due to a pathology suffered by the patient. The distal end 4 has an opening 6 connected to a longtudinal passage 8 called the drainage lumen for conducting drained fluids to the other or proximal end 10 of the catheter 1 where the drainage lumen 8 may be connected to a tube leading to a container, not shown, outside of the patient.

Adjacent the opening 6 at the distal end 4 is a retention balloon 12 completely surrounding and sealed to the shaft 3 of the catheter. An inflation lumen 14 in the shaft of the catheter leads from inside the balloon 12 lengthwise of the shaft to the inflation apparatus 2 which is usually in a branch 15 formed at the proximal end of the catheter to separate the drainage lumen 8 from the inflation lumen 14 at the end outside the patient.

While the distal end 4 is being inserted through the urethra and into the bladder, the retention balloon 12 is deflated and relaxed. After the distal end 4 and the balloon 12 have entered into the bladder, the inflation apparatus 2 is operated to allow fluid from a reservoir in or associated with the apparatus 2 to pass under sufficient pressure through the inflation lumen 14 to inflate the balloon 12 into a condition indicated by the dotted line 12c. Hereinafter, the relaxed or deflated condition of the balloon 12 will be indicated as 12a, a partially inflated condition will be indicated as 12b and a completely inflated condition as 12c.

A first embodiment of the improved inflation apparatus of this invention is shown in FIGS. 2, 2A and 2B in which reference numerals used in FIG. 1 are again used to indicate corresponding parts.

In this embodiment the inflation apparatus 2 includes a fluid reservoir 16 in the form of a squeezable, resilient, bulb- or ball-like enclosure made of a suitable material such as rubber or plastic. The reservoir 16 is connected by a restricted passage indicated at 17 to the inflation lumen 14 in the shaft 3 of the catheter and which in turn leads to the interior of a retention balloon 12 shown as in a deflated condition 12a adjacent the distal end 4. An opening 6 is located at the end 4 for the drainage of the patient's body fluids through the drainage lumen 8 extending to the proximal end 10 of the catheter.

The reservoir 16 is contained between the two parts 20 and 22 of a framework 23 which are hinged together at 24. The part 20 has a window 26 across which is secured in substantially flat condition an elastic membrane or diaphragm 28. The part 22 has a corresponding surface 30 which as shown is substantially rigid but which may also consist of another elastic diaphragm similar to diaphragm 28.

The reservoir 16 in its condition shown in FIG. 2 is filled with just enough fluid, preferably distilled water but which may also be a suitable gas, to inflate the retention balloon 12 when the fluid is expelled by squeezing the reservoir 16. Prior to squeezing the reservoir 16, the fluid is in an unpressurized condition so as to allow the retention balloon 12 to remain in a deflated condition indicated by 12a.

The catheter is inserted while the retention balloon is deflated. During or just after insertion, the parts 20 and 22 are brought together as shown in FIG. 2A to squeeze the reservoir 16 under the diaphragm 28. The diaphragm is stretched into the bulbous form shown in FIG. 2A and thereby exerts pressure to squeeze the reservoir 16 against the flat surface 30 of the part 22. The fluid then begins to be expelled into the retention balloon 12. Because the fluid must flow through the substantially restricted passage 17, expulsion of the fluid and inflation of the balloon is somewhat delayed.

The result is that although the parts 20 and 22 may be rapidly brought together and held closed, inflation takes place under controlled conditions allowing the operator to observe the condition of partial inflation 12b of the balloon as indicated by the bulbous condition of the membrane 28 and to make adjustments in the procedure as necessary. For instance, if inflation has commenced prematurely before proper insertion of the distal end 4 in the bladder, inflation may be interrupted or reversed by reopening the parts 20 and 22 to relieve the pressure on the membrane 28 and the reservoir 16.

The parts 20 and 22 may be held locked together by any suitable retention lock device such as a resilient catch 34 on the lower part 22 arranged to engage the edge of the upper part 20 to hold the two parts together.

When the fluid has been expelled from the reservoir 16 to inflate the retention balloon to the condition seen at 12c, the diaphragm 28 returns substantially to its original flattened condition as shown in FIG. 2B.

Thus it is seen that while inflation is initiated by closing of the parts 20 and 22 against the reservoir 16, the catheter is thereafter effectively self-inflating.

An alternate embodiment is shown in FIGS. 3, 3A and 3B. In this version an upper part 20a has a window 26a over which is arranged in an unstressed condition a flat membrane or diaphragm 28a. A lower part 22a may consist essentially of a flat substantially rigid surface, but it may also have as its operative surface another diaphragm like diaphragm 28a. A reservoir 16a in the form of a bulb, bag or ball is arranged between the parts 20a and 22a. Reservoir 16a may be made of a rubber or plastic material. The parts 20a and 22a are aligned by four pins or posts 24a mounted on part 22a and passing through holes in part 20a. Enlarged caps 24b on pins 24a retain part 20a in relation to part 22a. Other arrangements for holding the components assembled may be provided.

When it is desired to inflate the retention balloon 12, the parts 20a and 22a are brought axially together as seen in FIG. 3A. In other words, parts 20a and 22a are moved toward each other along an axis which is mutually perpendicular to the planes of parts 20a and 22a, while parts 20a and 22a remain substantially parallel to each other. For this purpose convenient protuberances 20b and 22b may be respectively provided on parts 20a and 22a for easy gripping of the parts between the thumbs and fingers of the operator. Parts 20a and 22a may be temporarily locked together as by overhanging detent parts 20c which resiliently engage the edges of the lower part 22a.

When the reservoir 16a is squeezed by bringing the parts 20a and 22a together, the diaphragm 28a is upwardly stretched as seen in FIG. 3A and the fluid begins to be expelled from the reservoir through restricted passage 17a to inflate the balloon as at 12b in FIG. 3A. When inflation of the balloon is complete as shown in FIG. 3B, the diaphragm 28a returns to a relatively flat position as also shown in FIG. 3B.

Because the inflation fluid remains unpressurized during storage prior to use, it does not tend to migrate through the walls of the reservoir as readily as if it were pre-pressurized. Therefore the reservoir parts may be made of thinner and less expensive material and a greater variety of materials is available for use.

The catheter balloon may be easily deflated and reinflated during use, and its condition of inflation is readily ascertainable by observation of the degree of distortion of the diaphragm.

I claim:

1. A self-inflating urinary catheter of the type which includes a retention balloon and an inflation lumen connected for conducting fluid to inflate the balloon wherein the improvement comprises a squeezable fluid reservoir connected to the inflation lumen, and means to squeeze the reservoir, said means including at least two parts of which one part includes a stretchable diaphragm adjacent the reservoir, said parts being arranged to be moved together with the reservoir between them thereby stretching the diaphragm and pressurizing the fluid, the stressed diaphragm exerting force on the fluid to expel it from the reservoir and through the inflation lumen to inflate the retention balloon.

2. A self-inflating urinary catheter according to claim 1 in which one of the parts has a window through which at least part of the stressed diaphragm is visible thereby providing an indication of the amount of fluid remaining in the reservoir before its expulsion to inflate the retention balloon.

3. A self-inflating urinary catheter according to claim 1 which includes a retention lock to hold the parts of the squeezing means together so as to maintain the diaphragm in a stretched and stressed condition against the reservoir.

4. A self-inflating urinary catheter according to claim 1 in which the said two parts are hinged together to form a framework, at least one of said parts having a window with the diaphragm secured in the window.

5. A self-inflating urinary catheter according to claim 1 in which the said two parts are arranged to be moved axially toward each other.

6. A self-inflating urinary catheter according to claim 1 which includes means by which to view the stressed diaphragm as an indication of the degree of expulsion of fluid from the reservoir.

7. A self-inflating urinary catheter according to claim 1 which includes a restricted passage between the reservoir and the retention balloon thereby providing an elapse of time between the initial stressing of the diaphragm and the completion of expulsion of the fluid from the reservoir into the balloon.

8. Apparatus for inflating the retention balloon at the distal end of a urinary catheter comprising:

a flexible reservoir connected to the proximal end of the catheter and communicating with the inflation lumen of the catheter, the reservoir containing an initially unpressurized inflation fluid; and means for compressing the reservoir to pressurize the inflation fluid in the reservoir and cause the fluid to flow from the reservoir through the inflation lumen to inflate the retention balloon, the means for compressing the reservoir including a substantially rigid frame member and an elastic membrane supported at its periphery by frame member, the frame member and the reservoir being moveable relative to one another so that the membrane presses against the surface of the reservoir causing the membrane to be distorted and stressed so that the membrane applies a compressive force to the reservoir.

9. The apparatus defined in claim 8 wherein the distortion of the membrane is visible to the operator of the catheter as an indication of the amount of inflation fluid remaining in the reservoir.

10. The apparatus defined in claim 9 wherein the inflation fluid must pass through a restricted passage between the reservoir and the retention balloon so that there is a delay between the time when the inflation fluid in the reservoir is fully pressurized and the time when the retention balloon is fully inflated.

11. The apparatus defined in claim 8 wherein the means for compressing the reservoir is releasable to remove the pressure on the fluid in the reservoir and allow the fluid in the retention ballon to flow back to the reservoir to deflate the retention balloon.

* * * * *